ies Patent [19]

United States Patent [19]

Brown et al.

[11] Patent Number: 4,683,232
[45] Date of Patent: Jul. 28, 1987

[54] HETEROCYCLIC COMPOUNDS HAVING CARDIOTONIC USE

[75] Inventors: David Brown, Macclesfield; Robert I. Dowell, Congleton; Rodney B. Hargreaves, Poynton; Brian G. Main, Sandbach, all of England

[73] Assignee: Imperial Chemical Industries PLC, London, England

[21] Appl. No.: 858,126

[22] Filed: May 1, 1986

Related U.S. Application Data

[62] Division of Ser. No. 675,741, Nov. 28, 1984, Pat. No. 4,587,246, which is a division of Ser. No. 528,103, Aug. 31, 1983, Pat. No. 4,503,054, which is a division of Ser. No. 321,899, Nov. 16, 1981, Pat. No. 4,423,045.

[30] Foreign Application Priority Data

Nov. 14, 1980 [GB] United Kingdom ............ 8036680

[51] Int. Cl.$^4$ ................ A61K 31/535; C07D 273/04
[52] U.S. Cl. ................................. 514/228; 514/229; 514/231; 514/232; 514/234; 544/68
[58] Field of Search ............... 544/68; 514/228, 229, 514/231, 232, 234

[56] References Cited

U.S. PATENT DOCUMENTS

| 3,314,455 | 5/1970 | Takamizawa | 544/8 |
|---|---|---|---|
| 3,377,345 | 4/1968 | Trepanier | 544/68 |
| 3,946,010 | 3/1976 | Wade | 544/182 |
| 4,097,425 | 1/1978 | Niznik | 544/68 |
| 4,105,848 | 8/1978 | Ellinger | 544/68 |
| 4,158,094 | 6/1979 | Niznik | 544/68 |
| 4,160,088 | 7/1979 | Niznik | 544/68 |
| 4,489,074 | 12/1984 | Brown et al. | 544/8 |
| 4,493,835 | 1/1985 | Hargreaves | 544/8 |

FOREIGN PATENT DOCUMENTS 62578 5/1984 Japan .

OTHER PUBLICATIONS

Ege et al., Liebigs Ann. Chem., pp. 791–799 (1977).
Holland, Recuel Trav. Chim., vol. 83, pp. 1047–1055 (1964).
Lempert-Sreter et al., Chemical Abstracts, vol. 88, entry 170106y (1978).

Primary Examiner—Richard L. Raymond
Attorney, Agent, or Firm—Cushman, Darby & Cushman

[57] ABSTRACT

Novel heterocyclic compounds of the formula:

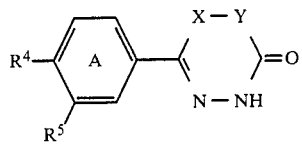

wherein either X is —CR$^1$R$^2$— and Y is oxygen, sulphur or —NR$^3$—, wherein R$^1$, R$^2$ and R$^3$, which may be the same or different, each is hydrogen or alkyl of up to 4 carbon atoms; or X is oxygen, sulphur or —NH— and Y is —CH$_2$—; wherein R$^4$ and R$^5$, which may be the same or different, each is hydrogen, cyano, nitro, amino or hydroxy, or alkylthio of up to 4 carbon atoms, or has various other meanings defined in claim 1, provided that R$^4$ and R$^5$ are not both hydrogen; or wherein R$^4$ and R$^5$ are joined together such that with the benzene ring A they form a benzheterocyclic ring as defined in claim 1; and therein the benzene ring A may optionally bear one or more further substituents; or a salt thereof where appropriate.

These compounds possess cardiotonic properties, and some of them possess peripheral vasodilator properties, and they are useful for the treatment of acute or chronic heart failure. Representative of the compounds is N,N-dimethyl-p-(5,6-dihydro-5-oxo-4H-1,3,4-thiadiazin-2-yl)benzamide. Also disclosed are processes for the manufacture of the compounds and pharmaceutical compositions containing them.

5 Claims, No Drawings

HETEROCYCLIC COMPOUNDS HAVING CARDIOTONIC USE

This is a division of application Ser. No. 675,741, filed Nov. 28, 1984, now U.S. Pat. No. 4,587,246, which is a division of Ser. No. 528,103 filed Aug. 31, 1983, now U.S. Pat. No. 4,503,054, which in turn is a division of Ser. No. 321,899 filed Nov. 16, 1981, now U.S. Pat. No. 4,423,045.

This invention relates to new heterocyclic compounds which possess cardiotonic properties.

Many 6-aryl-dihydropyridazin-3-one derivatives are known which possess pharmaceutical properties affecting the cardiovascular system. These are described, for example, in the Journal of Medicinal Chemistry, 1974, 17, 273–286 and in the Journal of Heterocyclic Chemistry, 1974, 11, 755–761, and there is much related patent literature.

When an additional hetero-atom is inserted into the pyridazine nucleus, most of the simple structures have been described in the academic chemical literature. Thus, for example:

1-phenyl-4H,6H-1,3,4-thiadiazin-5-one and its 6-methyl analogue are known from Chemical Abstracts, 1948, 42, 5919 and 1956, 50, 7817;

5-phenyl-3H,6H-1,3,4-thiadiazin-2-one and its 6-methyl analogue are known from Leibig's Annalen der Chemie, 1977, 791 and from this article are also known the corresponding p-bromophenyl and 4-biphenylyl analogues;

2-phenyl-4H,6H-1,3,4-oxadiazin-5-one is known from Receuil des Travaux chimiques des Pays Bas, 1929, 48, 417 and o-hydroxyphenyl analogues thereof are known from J. Heterocyclic Chemistry, 1970, 7, 927;

3-phenyl-4,5-dihydro-5-methyl-1H-1,2,4-triazin-6-one is known from J. Heterocyclic Chemistry, 1978, 15, 1271;

6-phenyl-4,5-dihydro-2H-1,2,4-triazin-3-one and its 4-methyl analogue are known from Chemical Abstracts, 1970, 73, 35334

From the patent literature 5-phenyl-3H,6H-1,3,4-oxadiazin-2-one and the corresponding 4-bromophenyl and 2-naphthyl analogues are known as blowing agents in the plastics industry, from U.S. Pat. Nos. 4,097,425, 4,105,848 and 4,158,094.

One of the abovementioned references discloses any pharmacological utility for any of the compounds described. The only references to pharmacological activity in this kind of compound of which applicants are aware appear in U.S. Pat. No. 3,514,455, which describes various 4,6-disubstituted-2-phenyl-4H,6H-1,3,4-thiadiazin-5-one derivatives which are claimed to possess antipyretic, analgesic, antiinflammatory and antiedema activities, and in U.S. Pat. No. 3,946,010, which describes various 3-o-aminophenyl-4,5 dihydro-1H-1,2,4-triazine-6-one derivatives which are claimed to possess antiinflammatory activity.

A compound of considerable interest at present as a cardiotonic agent is a pyridone derivative known by the name AMRINONE, which has the structure:

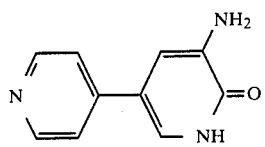

We have now found that various phenylthiadiazinone, oxadiazinone or triazinone derivatives which bear a substituent in the 3- or 4-position of the phenyl nucleus possess valuable cardiotonic properties.

According to the invention there is provided a heterocyclic compound of the formula:

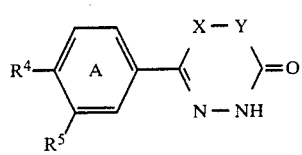

wherein
either X is —CR$^1$R$^2$— and Y is oxygen, sulphur or —NR$^3$—, wherein R$^1$, R$^2$ and R$^3$, which may be the same or different, each is hydrogen or alkyl or upto 4 carbon atoms;
or X is oxygen, sulphur or —NH— and Y is —CH$_2$—;
wherein
R$^4$ and R$^5$, which may be the same or different, each is hydrogen, cyano, nitro, amino or hydroxy, or alkylthio of up to 4 carbon atoms, or has the formula:

wherein Q is a direct link, or is imino (—NH—), or is oxyalkylene of up to 4 carbon atoms, wherein Z is oxygen or sulphur and wherein R$^6$, R$^7$, R$^8$ and R$^9$, which may be the same or different, each is hydrogen, alkyl, alkenyl, cycloalkyl or alkoxyalkyl each of up to 6 carbon atoms, or aryl or arylalkyl each of up to 12 carbon atoms, or wherein R$^7$ and R$^8$ together with the adjacent nitrogen atom form a 5- or 6-membered fully-saturated heterocyclic ring, provided that R$^4$ and R$^5$ are not both hydrogen;
or wherein R$^4$ and R$^5$ are joined together such that with the benzene ring A they form a benz-heterocyclic ring wherein the heterocyclic part is a 5- or 6-membered ring containing one oxygen, sulphur or nitrogen atom, and which heterocyclic part may optionally contain an oxo substituent or an alkyl or alkanoyl substituent each of up to 6 carbon atoms;
and wherein the benzene ring A may optionally bear one or more further substituents;
or a salt thereof where appropriate.

A suitable value for R$^1$, R$^2$ or R$^3$ when it is alkyl is, for example, methyl or ethyl A suitable value for R$^4$ or R$^5$ when it is alkylthio is, for example, methylthio or ethylthio.

A suitable value for Q when it is oxyalkylene is, for example, oxymethylene.

A suitable value for R$^6$, R$^7$, R$^8$ or R$^9$ when it is alkyl, alkenyl, cycloalkyl or alkoxyalkyl is, for example, methyl, ethyl, n-propyl, isopropyl, isobutyl, n-hexyl, allyl, cyclopentyl, cyclohexyl or methoxymethyl.

A suitable value for $R^6$, $R^7$, $R^8$ or $R^9$ when it is aryl or aralkyl is, for example, phenyl, tolyl, chlorophenyl, trichlorophenyl, benzyl or phenylethyl.

A suitable value for the heterocyclic ring formed by $R^7$, $R^8$ and the adjacent nitrogen atom is, for example, the pyrrolidino, piperidino or morpholino ring.

A suitable benz-heterocyclic ring formed by $R^4$, $R^5$ and the benzene ring A is, for example, the benzodioxole, indole, N-acetyl-2,3-dihydroindole or 2-oxo-2,3-dihydroindole ring.

Suitable optional further substituents in the benzene ring A, apart from the essential substituent(s) $R^4$ and/or $R^5$, are, for example, one or more chloro, bromo, methyl, ethyl, methoxy or ethoxy substituents.

An appropriate salt is a base-addition salt, for example an alkali metal, ammonium or amine salt, for example the sodium, potassium or benzylamine salt, of a heterocyclic compound of the invention wherein $R^6$ is hydrogen.

One preferred heterocyclic compound of the invention has the formula given above wherein either X is —CH$_2$— and Y is —NH—, or X is —CH$_2$—, —CHCH$_3$— or —C(CH$_3$)$_2$ and Y is sulphur, or X is oxygen or sulphur and Y is —CH$_2$—, wherein $R^4$ has the formula —COOR$^6$ or —CONR$^7$R$^8$ wherein $R^6$, $R^7$ and $R^8$ have the meanings stated above (that is, wherein Q is a direct link), wherein $R^5$ is hydrogen and wherein ring A bears no further substituent. A particularly preferred heterocyclic compound of this type is one wherein X is —CH$_2$— and Y is —NH—, or wherein X is sulphur and Y is —CH$_2$—.

A second preferred heterocyclic compound of the invention has the formula given above wherein either X is —CH$_2$—, —CHCH$_3$— or —C(CH$_3$)$_2$ and Y is sulphur, or X is —CH$_2$ and Y is oxygen, —NH— or —NCH$_3$—, or X is oxygen, sulphur or —NH— and Y is —CH$_2$—, wherein $R^4$ is hydrogen, wherein $R^5$ is cyano and wherein ring A bears no further substituent.

Specific heterocyclic compounds of the invention are hereinafter described in the Examples. Of these, preferred compounds are p-(5,6-dihydro-5-oxo-4H-1,3,4,thiadiazin-2-yl)benzoic acid and the methyl and isopropyl esters thereof; p-(5,6-dihydro-5-oxo-4H-1,3,4-thiadiazin-2-yl)benzamide, N-methylbenzamide and N,N-dimethylbenzamide; p-(5,6-dihydro-5-oxo-4H-1,3,4-oxadiazin-2-yl)benzamide; 6-m-cyanophenyl-4,5-dihydro-1,2,4-triazin-3(2H)-one; p-(2,3,4,5-tetrahydro-3-oxo-1,2,4-triazin-6-yl)benzamide, N-methylbenzamide, N-ethylbenzamide and N-n-propylbenzamide; 3-p-cyanophenyl-4,5-dihydro-1,2,4-triazin-6(1H)-one, p-(2,3-dihydro-2-oxo-6H-1,3,4-thiadiazin-5-yl)benzamide and N,N-dimethylbenzamide; and isopropyl p-(2,3-dihydro-2-oxo-6H-1,3,4-thiadiazin-5-yl)benzoate; and of these a particularly preferred compound is N,N-dimethyl-p-(5,6-dihydro-5-oxo-4H-1,3,4-thiadiazin-2-yl)benzamide.

A preferred process for the manufacture of a compound of the invention wherein X is oxygen or sulphur and Y is —CH$_2$— comprises the reaction of a hydrazide or thiohydrazide of the formula:

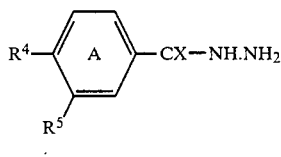

wherein $R^4$, $R^5$ and A have the meanings stated above and X is sulphur or oxygen, with an acid of the formula:

Hal—CH$_2$—COOH wherein Hal is a halogen atom, for example the chlorine or bromine atom, or with a reactive derivative thereof.

When X is sulphur the acid is preferably used directly, and the reaction may be carried out in aqueous solution, in the presence of a base, for example sodium hydroxide, at laboratory temperature.

When X is oxygen the acid is preferably used as a reactive derivative thereof, for example the acyl halide, and the reaction carried out in two stages. The benzoylhydrazine may be reacted with the acyl halide in an inert solvent, for example toluene, in the presence of a base, for example potassium carbonate. The diacyl hydrazine thus obtained may then be reacted with a base, for example sodium hydride, in a dipolar aprotic solvent, for example dimethylformamide, or with an alkali metal carbonate in acetone, and the reaction may be carried out at an elevated temperature, for example at about 100° C.

A preferred process for the manufacture of a compound of the invention wherein X is —CR$^1$R$^2$— and Y is sulphur comprises the reaction of a phenacyl halide of the formula:

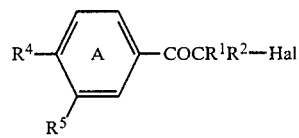

wherein $R^1$, $R^2$, $R^4$, $R^5$, A and Hal have the meanings stated above, with a thiocarbazate of the formula:

H$_2$N.NH.CS—O—R$^{10}$ or

H$_2$N.NH.CSO$^-$M$^+$ wherein $R^{10}$ is alkyl of up to 4 carbon atoms, for example methyl or ethyl, and wherein M$^+$ is an alkali metal or ammonium ion.

The reaction may be carried out in an organic diluent or solvent, for example acetonitrile or ethanol, at an elevated temperature, for example at the boiling point of the diluent or solvent.

A preferred process for the manufacture of a compound of the invention wherein X is —CR$^1$R$^2$— and Y is oxygen comprises the cyclisation of a compound of the formula:

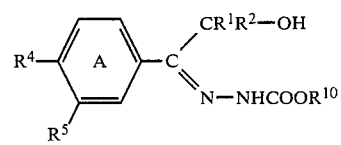

wherein A, $R^1$, $R^2$, $R^4$, $R^5$ and $R^{10}$ have the meanings stated above. The cyclisation may be carried out in the presence of a base, for example sodium ethoxide, in a diluent or solvent, for example ethanol, at laboratory temperature.

The starting material for the last-mentioned reaction may be obtained by the reaction of a compound of the formula:

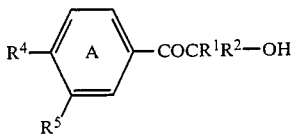

wherein A, $R^1$, $R^2$, $R^4$ and $R^5$ have the meanings stated above, with an alkyl carbazate of the formula:

$H_2N-NH.COOR^{10}$ wherein $R^{10}$ has the meaning stated above.

A preferred process for the manufacture of a compound of the invention wherein X is —NH— and Y is —$CH_2$— comprises the reaction of a compound of the formula:

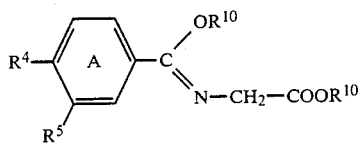

wherein A, $R^4$, $R^5$ and $R^{10}$ have the meanings stated above (the two $R^{10}$ substituents being the same or different alkyl radicals of up to 4 carbon atoms), with hydrazine.

The reaction may be carried out in a diluent or solvent, for example ethanol, at a temperature up to the boiling point of the diluent or solvent.

The starting material for the last-mentioned reaction may be obtained either by the reaction of a compound of the formula:

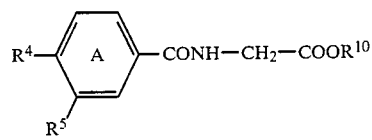

wherein A, $R^4$, $R^5$ and $R^{10}$ have the meanings stated above, with an oxonium trifluoroborate of the formula $(R^{10})_3OBF_4$ wherein $R^{10}$ has the meaning stated above, or by the reaction of a compound of the formula:

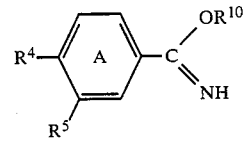

wherein A, $R^4$, $R^5$ and $R^{10}$ have the meanings stated above, with a salt of a glycine ester of the formula $H_2NCH_2COOR^{10}$, wherein $R^{10}$ has the meaning stated above.

A preferred process for the manufacture of a compound of the invention wherein X is —$CR^1R^2$— and Y is —NH— comprises the reaction of a compound of the formula:

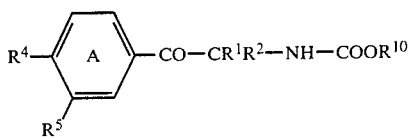

wherein A, $R^1$, $R^2$, $R^4$, $R^5$ and $R^{10}$ have the meanings stated above, with hydrazine.

The reaction may be carried out in a diluent or solvent, for example ethanol or isopropanol, at a temperature up to the boiling point of the diluent or solvent.

The starting material for the last-mentioned process may be obtained by the reaction of a compound of the formula:

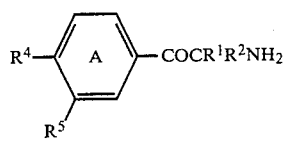

wherein A, $R^1$, $R^2$, $R^4$ and $R^5$ have the meanings stated above, with a chloroformate of the formula $R^{10}OCOCl$, wherein $R^{10}$ has the meaning stated above.

A compound wherein $R^4$ or $R^5$ is an amino substituent may be obtained by the the reduction of the corresponding compound wherein $R^4$ or $R^5$ is a nitro substituent or by the hydrolysis of the corresponding compound wherein Q is imino.

A compound wherein $R^4$ or $R^5$ is a carboxy substituent may be obtained by the hydrolysis of the corresponding compound wherein $R^4$ or $R^5$ is an alkoxycarbonyl or aminocarbonyl substituent.

A compound wherein $R^4$ or $R^5$ is a carboxy, carbamoyl or thiocarbamoyl substituent may be obtained by the hydrolysis, or reaction with hydrogen sulphide, of the corresponding compound wherein $R^4$ or $R^5$ is a cyano substituent.

A compound wherein $R^4$ or $R^5$ is a Q-containing substituent wherein Q is imino may be obtained by the acylation, or reaction with an isocyanate, of the corresponding amino-substituted compound.

A compound wherein $R^4$ or $R^5$ has the formula —Q—CZ—$OR^6$ or —Q—CZ—$NR^7R^8$, wherein Q is a direct link and Z is oxygen, may be obtained by the reaction of the corresponding compound wherein $R^4$ or $R^5$ is carboxy or an activated derivative thereof with an alcohol of the formula $R^6OH$ or an amine of the formula $HNR^7R^8$.

A compound wherein $R^4$ or $R^5$ has the formula —Q—CZ—$OR^6$ or —Q—CZ—$NR^7R^8$ wherein Q is oxyalkylene may be obtained by the reaction of the corresponding compound wherein $R^4$ or $R^5$ is hydroxy with a compound of the formula Hal-alk-CZ-$OR^6$, wherein Hal is a halogen atom and -alk- is an alkylene group of up to 4 carbon atoms, optionally followed by the conversion of the —CZ—$OR^6$ group to —CZ—$NR^7R^8$ by reaction with an amine of the formula $NHR^7R^8$.

A compound wherein $R^3$ is alkyl may be obtained by the alkylation of the corresponding compound wherein $R^3$ is hydrogen.

As stated above, a heterocyclic compound of the invention posesses cardiotonic activity. This may be demonstrated by its ability to increase the rate of change of aortic blood pressure in the anaesthetised cat. At a dose of the compound which produces an effective increase in said rate of change, that is, greater than a 25% increase, no symptom of toxicity is apparent.

Some of the heterocyclic compounds of the invention also possesses peripheral vasodilator activity, as demonstrated by their ability to increase the rate of flow in a perfused dog hind limb preparation.

The heterocyclic compound of the invention may be administered to warm-blooded animals, including man, in the form of a pharmaceutical composition comprising as active ingredient at least one heterocyclic compound of the invention in association with a pharmaceutically-acceptable diluent or carrier therefor.

A suitable composition is, for example, a tablet, capsule, aqueous or oily solution or suspension, emulsion, injectable aqueous or oily solution or suspension, dispersible powder, spray or aerosol formulation.

The pharmaceutical composition may contain, in addition to the heterocyclic compound of the invention, one or more drugs selected from sedatives, for example phenobarbitone, meprobamate, chlorpromazine and benzodiazepine sedative drugs, for example chlordiazepoxide and diazepam; vasodilators, for example hydralazine, glyceryl trinitrate, pentaerythritol tetranitrate and isosorbide dinitrate; diuretics, for example chlorothiazide, hydrochlorothiazide, amiloride, bendrofluazide or chlorthalidone; cardiac membrane stabilising agents, for example quinidine; agents used in the treatment of Parkinson's disease and other tremors, for example benzhexol; and cardiotonic agents, for example digitalis preparations.

When used for the treatment of acute or chronic heart failure in man, it is expected that the heterocyclic compound would be given to man at a total oral dose of between 100 mg. and 2000 mg. daily, at doses spaced at 6–8 hourly intervals, or at an intravenous dose of between 5 mg. and 100 mg.

Preferred oral dosage forms are tablets or capsules containing between 50 and 500 mg, and preferably 100 mg. or 500 mg., of active ingredient. Preferred intravenous dosage forms are sterile aqueous solutions of the heterocyclic compound containing between 0.05% and 1% w/w of active ingredient, and more particularly containing 0.1% w/v of active ingredient.

The invention is illustrated but not limited by the following Examples:

EXAMPLE 1

Bromoacetic acid (6.95 g.) was added to a stirred mixture of p-acetamidothiobenzohydrazide (10.45 g.) and aqueous 2N-sodium hydroxide solution (50 ml.), and the mixture was stirred at laboratory temperature for 75 minutes and the filtered through a filter aid. The filtrate was acidified to pH4 with acetic acid and the mixture was filtered. The solid product was crystallised from aqueous methanol and there was thus obtained N-[p-(5,6-dihydro-5-oxo-4H,-1,3,4-thiadiazin-2-yl)phenyl]acetamide, m.p. 266°–267° C.

The p-acetamidothiobenzohydrazide used as starting material was obtained as follows:

A stirred mixture of p-acetamidobenzaldehyde (57.0 g.), piperidine (52.5 ml.) and sulphur (flowers, 16.8 g.) was heated under reflux for 15 minutes. Further piperidine (40 ml.) was added and the mixture was stirred and heated under reflux for 1 hour and then poured into a mixture of ice and water. The mixture was filtered and the solid product was dried and crystallised from ethanol. There was thus obtained (p-acetamidothiobenzoyl)-piperidine, m.p. 201°–202° C.

A mixture of the above compound (52.4 g.), chloroform (200 ml.) and bromoacetic acid (29.2 g.) was kept at laboratory temperature for 18 hours and then filtered. There was thus obtained as solid residue N-(p-acetamido-α-carboxymethylthiobenzylidene)-piperidinium bromide, m.p. 123° C. (with decomposition).

Hydrogen sulphide was passed during 4 hours through an ice-cooled solution of the above compound (80.1 g.) in ethanol (250 ml.), and the mixture was kept at laboratory temperature for 18 hours and then poured slowly into ice-water (2 liters). The mixture was filtered and there was thus obtained as solid residue carboxymethyl p-acetamidodithiobenzoate, m.p. 224°–226° C.

Hydrazine hydrate (7.5 ml.) was added to a solution of the above compound (40.35 g.) in aqueous 2N-sodium hydroxide solution (75 ml.) and the mixture was kept at laboratory temperature for 30 minutes and then filtered. There was thus obtained as solid residue p-acetamidobenzthiohydrazide, m.p. 220°–221° C.

EXAMPLE 2

The process described in Example 1 was repeated using the appropriate thiobenzohydrazide as starting material. There were thus obtained the compounds shown in the following table:

| $R^4$ | $R^5$ | m.p.(°C.) | Crystallisation Solvent |
|---|---|---|---|
| H | nitro | 165–167 | ethanol/petroleum ether |
| hydroxy | H | 288–289 | dimethylformamide/diethyl ether |
| H | hydroxy | 215–217 | ethanol |
| amino | H | 192–197 | ethanol/petroleum ether |
| H | cyano | 193–197 | ethanol |
| carboxy | H | 306–308 (d) | dimethylformamide/diethyl ether |
| dimethyl-carbamoyl | H | 208 | isopropanol |

The starting thiohydrazides were prepared by a similar process to that described in the second part of Example 1. Intermediates that were characterised by melting point are shown in the tables below:

| $R^4$ | $R^5$ | m.p.(°C.) | m.p.(°C.) |
|---|---|---|---|
| H | nitro | 81–83 | |
| hydroxy | H | 169–170 | 179–180 |
| amino* | H | 162–164 | |
| H | cyano | 71–73 | 166–168 |
| carboxy | H | 222–223 | 198–199 |

-continued

R⁴—[phenyl with R⁵]—CS—N(ring)    R⁴—[phenyl with R⁵]—C(SCH₂COOH)=N⁺(ring) Br⁻

| R⁴ | R⁵ | m.p.(°C.) | m.p.(°C.) |
|---|---|---|---|
| dimethylcarbamoyl | H | 158 | 168 |

*Prepared by reduction of the corresponding 4-nitro compound (m.p. 164–167° C.) with aqueous ethanolic sodium sulphite solution at 80° C.

R⁴—[phenyl with R⁵]—CS—SCH₂COOH      R⁴—[phenyl with R⁵]—CSNHNH₂

| R⁴ | R⁵ | m.p. (°C.) | m.p. (°C.) |
|---|---|---|---|
| hydroxy | H | 193–197 | 203–205 (d) |
| amino | H | 127–130 | 168–169 |
| H | cyano | 113 | |
| carboxy | H | 218–221 | >310 |
| dimethylcarbamoyl | H | 158 | |

EXAMPLE 3

Phenyl chloroformate (6.89 g.) was added to a solution of 2-p-aminophenyl-4H,6H-1,3,4-thiadiazin-5-one (Example 2; 8.28 g.) in pyridine (40 ml.) and the mixture was kept at laboratory temperature for 1 hour, diluted with water and extracted with ethyl acetate. The extract was washed with water, dried and evaporated to dryness and the oily residue was stirred with petroleum ether. There was thus obtained 2-p-(phenoxycarboxyamido)phenyl-4H,6H-1,3,4-thiadiazin-5-one, m.p. 138°–142° C. A mixture of the above compound (3.27 g.), morpholine (1.0 g.) and dioxane (25 ml.) was heated at 100° C. for 2.5 hours, cooled and filtered, and the filtrate was slowly diluted with diethyl ether. The mixture was filtered and the solid product was crystallised from dioxane. There was thus obtained 4-[N-p-(5,6-dihydro-5-oxo-4H-1,3,4-thiadiazin-2-yl)phenylcarbamoyl]morpholine, m.p. 268°–269° C.

EXAMPLE 4

Methyl isocyanate (2 ml.) was added slowly to a solution of 2-p-aminophenyl-4H,6H-1,3,4-thiadiazin-5-one (Example 2; 3.1 g.) in boiling ethanol (100 ml.) and the mixture was heated under reflux for 30 minutes, cooled and filtered. There was thus obtained as solid product 1-methyl-3-p-(5,6-dihydro-5-oxo-4H-1,3,4-thiadiazin-2-yl)phenylurea, m.p. 275° C.

The process described above was repeated except that the appropriate isocyanate was used in place of methyl isocyanate. There were thus obtained the compounds described in the following table:

R⁷NHCONH—[phenyl]—C(=S-ring=O)N—NH

| R⁷ | m.p.(°C.) | Crystallisation Solvent |
|---|---|---|
| ethyl | 297–299 | dimethylformamide/diethyl ether |
| n-propyl | 250 | ethanol |
| allyl | 266 | ethanol |
| methoxymethyl | 220 | dimethylformamide/diethyl ether |

EXAMPLE 5

A mixture of 2-p-hydroxyphenyl-4H,6H-1,3,4-thiadiazin-5-one (Example 2; 10.9 g.), ethyl bromoacetate (8.35 g.), anhydrous potassium carbonate (6.9 g.) and dimethylformamide (50 ml.) was stirred at laboratory temperature for 2 hours and then poured into water. The mixture was extracted with ethyl acetate and the extract was washed with water, dried over magnesium sulphate and evaporated to dryness. The solid residue was crystallised from a mixture of ethyl acetate and petroleum ether, and there was thus obtained ethyl p-(5,6-dihydro-5-oxo-4H-1,3,4-thiadiazin-2-yl)phenoxyacetate, m.p. 142°–144° C.

A mixture of the above compound (2.94 g.), ethanol (10 ml.) and 33% ethanolic methylamine solution (9 ml.) was stirred for 2 hours and the filtered. The solid residue was crystallised from methanol and there was thus obtained N-methyl-p-(5,6-dihydro-5-oxo-4H-1,3,4-thiadiazin-2-yl)phenoxyacetamide, m.p. 212°–213° C.

The process described in the second paragraph above was repeated using the appropriate amine in place of methylamine, and there were thus obtained the compounds described in the following table:

R⁷R⁸NCOCH₂O—[phenyl]—C(=S-ring=O)N—NH

| R⁷ | R⁸ | m.p. (°C.) | Crystallisation Solvent |
|---|---|---|---|
| ethyl | H | 216–217 | methanol |
| n-propyl | H | 202–203 | methanol |
| methyl | methyl | 199–200 | aqueous dimethylformamide |
| benzyl | H | 192–194 | methanol |

EXAMPLE 6

A mixture of 2-m-hydroxyphenyl-4H,6H-1,3,4-thiadiazin-5-one (Example 2; 1.0 g.), ethyl bromoacetate (0.61 ml.), ethanol (25 ml.) and sodium hydrogen carbonate (0.84 g.) was heated under reflux for 48 hours and then evaporated to dryness. The residue was dissolved in a 9:1 v/v mixture of chloroform and methanol and chromatographed on silica gel (100 g.) using the same solvent mixture as eluant. The fractions of eluate containing a product having an $R_f$ of 0.7 on silica gel plates using the same solvent mixture were combined and evaporated to dryness, and the residue was crystallised from ethanol. There was thus obtained ethyl m-(5,6-dihydro-5-oxo-4H-1,3,4-thiadiazin-2-yl)phenoxyacetate, m.p. 113°–115° C.

A mixture of the above compound (1.5 g.) and 33% ethanolic methylamine (25 ml.) was heated under reflux for 18 hours and then evaporated to dryness, and the residue was crystallised from a 25:1 v/v mixture of ethanol and dimethylformamide. There was thus obtained N-methyl-m-(5,6-dihydro-5-oxo-4H,-1,3,4-thiadiazin-2-yl)phenoxyacetamide, m.p. 195°–197° C.

EXAMPLE 7

N,N¹-dicyclohexylcarbodi-imide (19.5 g.) was added to a stirred solution of p-(5,6-dihydro-5-oxo-4H-1,3,4-thiadiazin-2-yl)benzoic acid (Example 2; 21.24 g.), trichlorophenol (20.8 g.) and pyridine (7.25 ml) in ethyl acetate (500 ml.) and the mixture was stirred for 16 hours. Acetic acid (10 ml.) was added, the mixture was filtered and the solid residue was washed well with ethyl acetate. The combined filtrate and washings were evaporated to dryness and the residue was crystallised from a mixture of methanol and dimethylformamide. There was thus obtained 2,4,5-trichlorophenyl p-(5,6-dihydro-5-oxo-4H-1,3,4-thiadiazin-2-yl)benzoate, m.p. 220°–222° C.

A 33% w/v solution of dimethylamine in ethanol (40 ml.) was added to a solution of the above compound (30. g.) in dimethylformamide (150 ml.) and the mixture was kept at laboratory temperature for 1 hour and then diluted with water and filtered. The solid product was dried and crystallised from isopropanol and there was thus obtained N,N-dimethyl-p-(5,6-dihydro-5-oxo-4H-1,3,4-thiadiazin-2-yl)benzamide, m.p. 208° C.

The process described above was repeated using the appropriate amine in place of dimethylamine, and there were thus obtained the compounds described in the following table:

| R⁷ | R⁸ | m.p. (°C.) | Crystallisation Solvent |
|---|---|---|---|
| H | H | 268–270 | isopropanol |
| methyl | H | 236–237 | ethanol |
| ethyl | H | 222–224 | methanol |
| n-propyl | H | 236–237 | ethanol/diethyl ether |
| allyl | H | 227–229 | isopropanol |
| benzyl | H | 219–220 | isopropanol |
| cyclohexyl | H | 245–246 | isopropanol |
| methyl | ethyl | 125–126 | (purified by chromatography) |
| ethyl | ethyl | 154–155 | isopropanol |
| —(CH₂)₂—O—(CH₂)₂— | | 180–181 | ethanol |
| —(CH₂)₅— | | 163–166 | methanol |

EXAMPLE 8

A mixture of p-(5,6-dihydro-5-oxo-4H-1,3,4-thiadiazin-2-yl)benzoic acid (Example 2; 0.5 g.), concentrated sulphuric acid (0.25 ml.) and isopropanol (100 ml.) was heated under reflux for 36 hours, concentrated by distilling off 70 ml. of the isopropanol, cooled and filtered. The solid residue was crystallised from methanol and there was thus obtained isopropyl p-(5,6-dihydro-5-oxo-4H-1,3,4-thiadiazin-2-yl)benzoate, m.p. 141°–143° C.

The process described above was repeated using the appropriate alcohol in place of isopropanol, and there were thus obtained the compounds described in the following table:

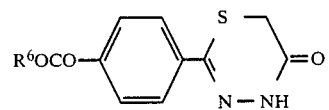

| R⁶ | m.p. (°C.) | Crystallisation Solvent |
|---|---|---|
| methyl | 205–206 | methanol |
| n-propyl | 148–150 | methanol |

EXAMPLE 9

A mixture of p-(5,6-dihydro-5-oxo-4H-1,3,4-thiadiazin-2-yl)benzoic acid (Example 2; 1.18 g.) 1-hydroxybenzotriazole (0.72 g.), aniline (0.47 g.) and dimethylformamide (25 ml.) was stirred at laboratory temperature for 45 minutes, dicyclohexylcarbodi-imide (1.6 ml.) was added and the mixture was stirred at laboratory temperature for 15 hours and then evaporated to dryness under reduced pressure. The residue was stirred with diethyl ether, the mixture was filtered and the solid residue was crystallised from ethanol. There was thus obtained N-phenyl-p-(5,6-dihydro-5-oxo-4H-1,3,4-thiadiazin-2-yl)benzamide, m.p. 264°–266° C.

The process described above was repeated except that n-butanol or isobutanol was used in place of aniline. There were thus obtained n-butyl p-(5,6-dihydro-5-oxo-4H-1,3,4-thiadiazin-2-yl)benzoate, m.p. 185°–188° C. after crystallisation from ethyl acetate/diethyl ether, and isobutyl p-(5,6-dihydro-5-oxo-4H-1,3,4-thiadiazin-2-yl)benzoate, m.p. 166°–168° C. after crystallisation from ethyl acetate.

EXAMPLE 10

A mixture of p-(5,6-dihydro-5-oxo-4H-1,3,4-thiadiazin-2-yl)benzoic acid (Example 2; 0.5 g.) and dimethylformamide (30 ml.) was stirred at laboratory temperature for 15 minutes, aqueous 2N-sodium hydroxide solution (1.06 ml.) was added and the mixture was evaporated to dryness. The residue was stirred with methanol, the mixture was filtered and the solid salt was purified by dissolution in water and precipitation from solution with ethanol. There was thus obtained sodium p-(5,6-dihydro-5-oxo-4H-1,3,4-thiadiazin-2-yl)benzoate, m.p. >300° C.

EXAMPLE 11

A mixture of p-amino-2-chloroacetophenone (16.95 g.), methoxythiocarbonylhydrazine (15.9 g.) and acetonitrile (300 ml.) was heated under reflux for 3 hours and then filtered. The filtrate was cooled and filtered, and the solid product was crystallised from acetonitrile.

There was thus obtained 5-p-aminophenyl-3H,6H-1,3,4-thiadiazin-2-one, m.p. 233°-235° C.

The process described above was repeated using the appropriately substituted 2-chloroalkanophenone as starting material, and there were thus obtained the compounds described in the following table:

$$R^4 \diagdown \underset{R^5}{A} \diagup \overset{R^1}{\underset{N-NH}{\overset{|}{C}}} \diagdown \overset{S}{\underset{}{\diagup}} = O$$

| $R^1$ | $R^4$ | $R^5$ | Other Ring A Substituent | m.p. (°C.) | Crystallisation Solvent |
|---|---|---|---|---|---|
| H | H | cyano | — | 191-192 | ethanol |
| H | amino | H | 3-chloro | 150-152 | isopropanol |
| H | acetamido | H | — | 238 | ethanol/dimethylformamide |
| H* | carboxy | H | — | 298-300 | methanol |
| H* | N—methylcarbamoylmethoxy | H | — | 198-200 | methanol |
| H* | N—benzylcarbamoylmethoxy | H | — | 185-188 with decomposition | methanol |
| H* | carbamoyl | H | — | 255-257 | methanol |
| H* | amino | H | 3,5-dichloro | 173-175 | acetonitrile |
| H* | nitro | H | — | 224-226 | ethanol |
| methyl | H | cyano | — | 188-190 | methanol |
| methyl | H | cyano | 2-methyl | 168-169 | methanol |
| methyl | amino | H | — | 199-201 | acetonitrile |
| methyl*+ | acetamido | H | — | 201-204 | (purified by chromatography) |
| H | methylenedioxy | | — | 119 | (purified by chromatography) |
| H | —N(COCH₃)—CH₂CH₂— | | — | 238-245 | acetonitrile |
| methyl | methylenedioxy | | — | 121 | isopropanol/water |

*The corresponding 2-bromoalkanophenone was used in place of the 2-chloroalkanophenone.

+ The starting material was obtained as follows:
A solution of p-acetamidopropiophenone (1.91 g.) in hot chloroform (10 ml.) was added to a stirred mixture of finely ground copper (II) bromide (4.01 g.) and ethyl acetate (10 ml.) which was heated under reflux, and the mixture was stirred and heated under reflux for 3 hours, cooled and filtered. The filtrate was evaporated to dryness and the residue was stirred with water. The mixture was filtered and the solid product was crystallised from acetonitrile. There was thus obtained p-acetamido-2-bromopropiophenone, m.p. 120-121° C.

EXAMPLE 12

A mixture of S-(1-m-cyanobenzoyl-1-methyl)ethyl thiocarbazate (1.0 g.), concentrated aqueous hydrochloric acid (0.5 ml.) and ethanol (15 ml.) was heated under reflux for 30 minutes and then evaporated to dryness under reduced pressure. The residue was crystallised from ethanol and there was thus obtained 5-m-cyanophenyl-6,6-dimethyl-3H,6H-1,3,4-thiadiazine-2-one, m.p. 140°-142° C.

The thiocarbazate used as starting material was obtained as follows:

A solution of ammonium thiocarbazate (4.9 g.) in a mixture of water (20 ml.) and ethanol (50 ml.) was added to a solution of 1-bromo-1-methylethyl m-cyanophenyl ketone (7.6 g.) in ethanol (10 ml.) and the mixture was stirred at laboratory temperature for 20 hours and then filtered. The solid product was crystallised from ethanol and there was thus obtained S-(1-m-cyanobenzoyl-1-methyl)ethyl thiocarbazate, m.p. 179°-181° C. (with decomposition).

EXAMPLE 13

The process described in Example 4 was repeated except that 5-p-aminophenyl-3H,6H-1,3,4-thiadiazin-2-one or the corresponding 6-methyl derivative thereof (Example 11) and the appropriate isocyanate were used as starting materials. There were thus obtained the compounds shown in the following table:

$$R^7NHCONH \diagdown \bigcirc \diagup \overset{R^1}{\underset{N-NH}{\overset{|}{C}}} \diagdown \overset{S}{\underset{}{\diagup}} = O$$

| $R^7$ | $R^1$ | m.p. (°C.) | Crystallisation Solvent |
|---|---|---|---|
| methyl | H | 250-251 | ethanol |
| n-propyl | H | 208-210 | acetonitrile |
| n-hexyl | H | 183 | ethanol |
| methyl | methyl | 222-224 | acetonitrile |
| n-propyl | methyl | 215 | acetonitrile |

EXAMPLE 14

A mixture of 5-p-aminophenyl-3H,6H-1,3,4-thiadiazin-2-one (Example 11; 2.07 g.), methanesulphonyl chloride (1.34 g.) and ethanol (100 ml.) was heated under reflux for 5 hours and then evaporated to dryness under reduced pressure. The residue was stirred with acetonitrile, the mixture was filtered and the solid residue was dissolved in hot dimethylformamide (20 ml.) Acetonitrile was added until crystallisation began, and the mixture was allowed to cool and was then filtered. There was thus obtained as solid product N-[p-2,3-dihydro-2-oxo-6H-1,3,4-thiadiazin-5-yl)phenyl]methanesulphonamide, m.p. 204°-206° C.

The process described above was repeated except that phenylacetyl chloride was used in place of methanesulphonyl chloride, and that the reaction was carried out at laboratory temperature in acetone solution in the presence of triethylamine. There was thus obtained N-[p-(2,3-dihydro-2-oxo-6H-1,3,4-thiadiazin-5-yl)phenyl]phenylacetamide, m.p. 233° C. after crystallisation from acetonitrile.

EXAMPLE 15

A mixture of p-(2,3-dihydro-2-oxo-6H-1,3,4-thiadiazin-5-yl)benzoic acid (Example 11; 0.5 g.) and thionyl chloride (5 ml.) was heated under reflux for 30 minutes and the excess of thionyl chloride was removed by evaporation under reduced pressure. Isopropanol (5 ml.) was added and the mixture was heated under reflux for 30 minutes, cooled and filtered. The solid residue was crystallised from isopropanol and there was thus obtained isopropyl p-(2,3-dihydro-2-oxo-6H-1,3,4-thiadiazin-5-yl)benzoate, m.p. 159°-161° C.

The process described above was repeated using the appropriate alcohol or amine as starting material in place of isopropanol, and there were thus obtained the compounds described in the following tables:

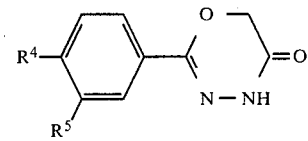

| R⁶ | m.p. (°C.) | Crystallisation Solvent |
|---|---|---|
| methyl | 194–196 | methanol |
| ethyl | 149–151 | ethanol |
| n-propyl | 124–126 | methanol |
| isobutyl | 158–159 | methanol |

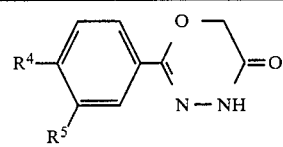

| R⁷ | R⁸ | m.p. (°C.) | Crystallisation Solvent |
|---|---|---|---|
| methyl | methyl | 218–219 | ethanol |

EXAMPLE 16

Sodium hydride (500 mg. of a 50% suspension in mineral oil) was added to a solution of N-m-cyanobenzoyl-N¹-chloroacetylhydrazine (2.3 g.) in dimethylformamide (40 ml.) and the mixture was heated at 100° C. for 2 hours, cooled, diluted with water and acidified to pH 1 with aqueous hydrochloric acid. The mixture was extracted with ethyl acetate and the extract was washed with water, dried and evaporated to dryness. The residue was crystallised from ethyl acetate and there was thus obtained 2-m-cyanophenyl-4H,6H-1,3,4-oxadiazin-5-one, m.p. 229°–230° C.

The diacylhydrazine used as starting material was obtained as follows:

A mixture of ethyl m-cyanobenzoate (10.6 g.) hydrazine hydrate (6.0 ml.) and ethanol (100 ml.) was heated under reflux for 4 hours, cooled and filtered. The solid hydrazide (5.6 g.) was washed with ethanol and dried, and then suspended in toluene (100 ml.). Anhydrous potassium carbonate (4.5 g.) was added to the stirred suspension, followed by chloroacetyl chloride (4.0 g.) added dropwise, and the mixture was stirred for 30 minutes and then washed with water. The toluene solution was then evaporated to dryness and there was thus obtained as residue N-m-cyanobenzoyl-N¹-chloroacetylhydrazine, which was used without further purification.

EXAMPLE 17

The process described in Example 16 was repeated except that the appropriate ethyl benzoate was used as initial starting material in place of ethyl m-cyanobenzoate, and that dioxan was used as solvent in place of toluene, and triethylamine was used as base in place of potassium carbonate in the preparation of the diacylhydrazine. There were thus obtained the compounds described in the following table:

| R⁴ | R⁵ | m.p. (°C.) | Crystallisation Solvent |
|---|---|---|---|
| nitro | H | 220–222 | ethanol |
| cyano | H | 261–264 | acetone |
| dimethylaminosulphonyl | H | 249–254 | methanol |
| H | methylthio | 142–144 | methanol |
| H | methanesulphonyl | 218–220 | methanol |
| H | dimethylaminosulphonyl | 202–205 | methanol/petroleum ether |

EXAMPLE 18

A stirred mixture of N-m-methylsulphamoylbenzoyl-N¹-chloroacetylhydrazine (0.2 g.), potassium carbonate (0.09 g.) and acetone (10 ml.) was heated under reflux for 16 hours and then filtered, and the filtrate was evaporated to dryness. The residue was crystallised from methanol and there was thus obtained N-methyl-m-(5,6-dihydro-5-oxo-4H-1,3,4-oxadiazin-2-yl)benzenesulphonamide, m.p. 227°–229° C.

The process described above was repeated using the appropriate diacylhydrazine and there were thus obtained the compounds described in the following table, all of which were crystallised from methanol:

| R⁴ | R⁵ | m.p. (°C.) |
|---|---|---|
| H | carbamoyl | 278–280 |
| H | sulphamoyl | 237–238 Quarter-hydrate |
| sulphamoyl | H | 249–251 |
| dimethylcarbamoyl | H | 203–204 |

EXAMPLE 19

A solution of 2-p-nitrophenyl-4H,6H-1,3,4-oxadiazin-5-one (Example 17; 2.2 g.) in ethyl acetate (250 ml.) was hydrogenated in the presence of a 5% palladium-on-charcoal catalyst at laboratory temperature and atmospheric pressure until 670 ml. of hydrogen has been absorbed. The mixture was filtered and the filtrate was evaporated to dryness. There was thus obtained as solid residue 2-p-aminophenyl-4H,6H-1,3,4-oxadiazin-5-one, m.p. 253°–255° C. (with decomposition).

EXAMPLE 20

The process described in Example 4 was repeated except that 2-p-aminophenyl-4H,6H-1,3,4-oxadiazin-5-one (Example 19) was used as starting material. There was thus obtained 2-p-(3-methylureido)phenyl-4-methyl-3-p-(5,6-dihydro-5-oxo-4H-1,3,4-oxadiazin-2- yl)phenylurea, m.p. 298°–300° C. after crystallisation from ethanol.

EXAMPLE 21

Hydrogen peroxide (2 ml. of a 30% v/v aqueous solution) was added dropwise to a stirred mixture of 2-p-cyanophenyl-4H,6H-1,3,4-oxadiazin-5-one (Example 17; 0.25 g.), anhydrous potassium carbonate (0.86 g.), acetone (12.5 ml.) and water (2.5 ml.) which was kept at 20° C., and the mixture was stirred for a further 18 hours and then filtered. The solid residue was crystallised from methanol and there was thus obtained p-(5,6-dihydro-5-oxo-4H-1,3,4-oxadiazin-2-yl)benzamide, m.p. 295°–298° C.

EXAMPLE 22

Sodium ethoxide (0.5 g.) was added to a stirred solution of 2-hydroxyaceto-(m-cyanophenone) $N^1$-ethoxycarbonylhydrazone (0.2 g.) in ethanol (5 ml.) and the mixture was stirred at laboratory temperature for 60 hours and then filtered. The solid product was crystallised from ethyl acetate and there was thus obtained 5-m-cyanophenyl-3H,6H-1,3,4-oxadiazin-2-one, m.p. 204°–208° C.

The 2-hydroxyaceto-(m-cyanophenone) $N^1$-ethoxycarbonylhydrazone used as starting material was obtained as follows:

A mixture of m-cyanophenacyl bromide (5.3 g.), potassium acetate (3.47 g.) and acetic acid (30 ml.) was heated under reflux for 2 hours, cooled, diluted with water and extracted with ethyl acetate. The extract was washed with water, dried and evaporated to dryness and the residue was crystallised from ethanol. Concentrated aqueous hydrochloric acid (0.5 ml.) was added to a solution of the 2-acetoxy-aceto-(m-cyanophenone) thus obtained (2.5 g.) in methanol and the mixture was heated under reflux for 2 hours and then evaporated to dryness. The residue was stirred with diethyl ether and the mixture was filtered. There was thus obtained as solid residue 2-hydroxyaceto-(m-cyanophenone), m.p. 121°–122° C.

Ethyl carbazate (0.25 g.) and concentrated aqueous hydrochloric acid (0.5 ml.) were added to a solution of the above compound (0.4 g.) in ethanol (20 ml.) and the mixture was stirred for 16 hours at laboratory temperature and then filtered. The solid residue was crystallised from ethyl acetate and there was thus obtained 2-hydroxyaceto-(m-cyanophenone) $N^1$-ethoxycarbonylhydrazone, m.p. 146°–147° C.

EXAMPLE 23

A mixture of ethyl n-nitrohippurate (26.5 g.), triethyloxonium fluoroborate (140 ml. of a 2.3 molar solution in methylene chloride) and methylene chloride (400 ml.) was stirred at laboratory temperature for 18 hours. A solution of potassium carbonate (50 g.) in water (50 ml.) was added, the mixture was shaken, and the organic phase was separated, dried and evaporated to dryness. The residue was stirred with petroleum ether and the mixture was filtered. The filtrate was evaporated to dryness and the residual ethyl N-(ethoxycarbonylmethyl)-p-nitrobenzimidate (22.1 g.) was dissolved in ethanol (600 ml.). Hydrazine hydrate (10 ml.) was added and the mixture was heated under reflux for 4.5 hours, cooled and filtered. There was thus obtained as solid product 3-p-nitrophenyl-4,5-dihydro-1H-1,2,4-triazine-6-one, m.p. 284°–286° C.

The process described above was repeated except that the appropriate ethyl hippurate was used as starting material in place of ethyl p-nitrohippurate. There were thus obtained the compounds described in the following table:

| $R^4$ | $R^5$ | m.p. (°C.) | Crystallisation Solvent |
|---|---|---|---|
| cyano | H | >300 | methanol |
| benzoyl | H | 270–273 | n-propanol |
| acetyl | H | 223–225 | (purified by chromatography) |
| H | cyano | 256–257 | methanol |

EXAMPLE 24

Dry hydrogen chloride was passed through a mixture of ethyl 2-p-cyanophenoxyacetate (30.75 g.), diethyl ether (500 ml.) and ethanol (10 ml.) at 0°–5° C. until the solution was saturated with hydrogen chloride, and the mixture was kept at 0° C. for 3 days and then filtered. There was thus obtained as solid residue ethyl p-(ethoxycarbonylmethoxy)benzimidate hydrochloride, m.p. 124°–126° C. A mixture of this compound (6.51 g.), diethyl ether (100 ml.) and a solution of potassium carbonate (3.6 g.) in water (15 ml.) was shaken, the ethereal phase was separated and to it was added a solution of ethyl glycinate hydrochloride (3.1 g.) in water (10 ml.). The mixture was stirred at laboratory temperature for 45 hours and the organic phase was separated, washed with water, dried and evaporated to dryness. The residual oil, which consisted of ethyl N-(ethoxycarbonylmethyl)-p-(ethoxycarbonylmethoxy)benzimidate (5.8 g.) was dissolved in ethanol (75 ml.) hydrazine hydrate (1 ml.) was added and the mixture was heated under reflux for 18 hours and then evaporated to dryness. The residue was purified by chromatography on silica gel using chloroform containing increasing amounts (up to 5% v/v) of ethanol as eluant. There was thus obtained ethyl p-(1,4,5,6-tetrahydro-6-oxo-1,2,4-triazin-3-yl)phenoxyacetate, m.p. 135° C.

The process described above was repeated using the appropriate ethyl phenoxyacetate in place of ethyl 2-p-cyanophenoxyacetate, and there were thus obtained the compounds described in the following table:

| $R^4$ | $R^5$ | m.p. (°C.) | Crystallisation Solvent |
|---|---|---|---|
| isopropoxycarbonyl | H | 233–236 | ethanol |
| H | dimethylcarbamoyl | 218–221 | methanol/diethyl ether |
| H | methoxycarbonyl | 181–183 | ethyl acetate |
| methylenedioxy | | 223–225 | ethanol |

EXAMPLE 25

The process described in Example 19 was repeated except that 3-p-nitrophenyl-4,5-dihydro-1H-1,2,4-triazin-6-one (Example 23) was used as starting material. There was thus obtained 3-p-aminophenyl-4,5-dihydro-6H-1,2,4-triazin-6-one, m.p. 241°–244° C. after crystallisation from a mixture of dimethylformamide and diethyl ether.

EXAMPLE 26

The process described in Example 4 was repeated except that 3-p-aminophenyl-4,5-dihydro-1H-1,2,4-triazin-6-one (Example 25) was used as starting material. There was thus obtained 1-methyl-3-p-(1,4,5,6-tetrahydro-6-oxo-1,2,4-triazin-3-yl)phenylurea, m.p. 248°–249° C. after crystallisation from ethanol.

EXAMPLE 27

A mixture of 3-p-aminophenyl-4,5-dihydro-1H-1,2,4-triazin-6-one (Example 25; 0.57 g.), acetic anhydride (0.3 ml.) and toluene (50 ml.) was heated under reflux for 90 minutes, cooled and filtered. The solid product was crystallised from ethanol and there was thus obtained N-[p-(1,4,5,6-tetrahydro-6-oxo-1,2,4-triazin-3-yl)phenyl]acetamide, m.p. 300° C.

EXAMPLE 28

The process described in the second part of Example 5 was repeated using ethyl p-(1,4,5,6-tetrahydro-6-oxo-1,2,4-triazin-3-yl)phenoxyacetate (Example 24) and either benzylamine or dimethylamine as starting materials. There were thus obtained N-benzyl-p-(1,4,5,6-tetrahydro-6-oxo-1,2,4-triazin-3-yl)phenoxyacetamide, m.p. 136°–140° C. after crystallisation from ethanol. and N,N-dimethyl-p-(1,4,5,6-tetrahydro-6-oxo-1,2,4-triazin-3-yl)phenoxyacetamide, m.p. 254°–257° C. after crystallisation from methanol.

EXAMPLE 29

The process described in Example 21 was repeated except that 3-p-cyanophenyl-4,5-dihydro-1H-1,2,4-triazin-6-one (Example 23) was used as starting material. There was thus obtained p-(1,4,5,6-tetrahydro-6-oxo-1,2,4-triazin-3-yl)benzamide, m.p. >300° C. after crystallisation from aqueous acetone.

EXAMPLE 30

A mixture of isopropyl p-(1,4,5,6-tetrahydro-6-oxo-1,2,4-triazin-3-yl)benzoate (Example 24; 0.5 g.), methanol (50 ml.) and 30% w/v methanolic potassium hydroxide solution (1 ml.) was heated under reflux for 30 minutes and then evaporated to dryness. The residue was dissolved in water and the solution acidified to pH 1 with concentrated aqueous hydrochloric acid and then filtered. The solid residue was purified by redissolution in aqueous potassium hydroxide solution and reprecipitation with hydrochloric acid. There was thus obtained p-(1,4,5,6-tetrahydro-6-oxo-1,2,4-triazin-3-yl)benzoic acid, m.p. >300° C.

EXAMPLE 31

A stirred mixture of ethyl N-(2-p-acetamidophenyl-2-oxoethyl)carbamate (2.11 g.), hydrazine hydrate (4 ml.), water (20 ml.) and ethanol (2 ml.) was heated under reflux for 17 hours, cooled and filtered. The solid product was crystallised from ethanol and then from acetic acid, and there was thus obtained N-[p-(2,3,4,5-tetrahydro-3-oxo-1,2,4-triazin-6-yl)phenyl]acetamide, m.p. 280°–284° C. (with decomposition).

The ethyl carbamate used as starting material was obtained as follows:

A solution of bromine (5.83 ml.) in chloroform (40 ml.) was added to a stirred solution of p-acetamidoacetophenone (25.6 g.) in chloroform (200 ml.) and the mixture was stirred for 1 hour and then filtered. The residue was crystallised from isopropanol and there was thus obtained p-acetamidophenacyl bromide, m.p. 182°–184° C.

A solution of sodium azide (40 g.) in water (125 ml.) was added slowly to a stirred solution of the above bromide (56 g.) in dioxan (500 ml.) which was heated to 60° C., and the mixture was stirred and heated at that temperature for 30 minutes. Water (1.2 liters) was added and the mixture was allowed to cool and was then filtered. The solid residue was crystallised from ethanol and there was thus obtained p-acetamidophenacyl azide, m.p. 170° C. (with decomposition).

A mixture of the above azide (14.5 g.), ethanol (100 ml.), chloroform (100 ml.), concentrated aqueous hydrochloric acid (7.5 ml.) and a 30% palladium-on-charcoal catalyst (1 g.) was shaken with hydrogen at laboratory temperature and atmospheric pressure until all the azide had been reduced (the reaction was followed by thin layer chromatography on silica gel plates using a 9:1 v/v mixture of chloroform and methanol as developing solvent). The mixture was filtered and the solid residue was stirred with water (100 ml.). The mixture was filtered and the filtrate was evaporated to dryness. The solid product was crystallised from aqueous ethanol and there was thus obtained 2-(p-acetamidophenyl)-2-oxoethylamine hydrochloride, m.p. 215° C. (with decomposition).

A solution of ethyl chloroformate (6.6 ml.) in diethyl ether (20 ml.) was added to a stirred mixture of the above hydrochloride (14.2 g.), water (80 ml.), pyridine (11.5 ml.) and diethyl ether 20 ml.), and the mixture was stirred for 3 hours and then filtered. The solid product consisted of ethyl N-(2-p-acetamidophenyl-2-oxoethyl)-carbamate, m.p. 164°–166° C.

EXAMPLE 32

The process described in Example 31 was repeated except that ethyl N-(2-m-nitrophenyl-2-oxo-ethyl)carbamate was used as starting material. There was thus obtained 6-m-nitrophenyl-4,5-dihydro-2H-1,2,4-triazin-3-one, m.p. 288° C. (with decomposition) after crystallisation from acetic acid.

The ethyl N-(2-m-nitrophenyl-2-oxoethyl)carbamate used as starting material was prepared from the corresponding 2-m-nitrophenyl-2-oxoethylamine hydrochloride by a similar process to that described in the second part of Example 31. The ethylamine hydrochloride was prepared as follows:

A solution of m-nitrophenacyl bromide (25 g.; m.p. 90°–92° C.; prepared by a similar process to that described in the second part of Example 31) in warm chloroform (95 ml.) was added to a stirred solution of hexamethylenetramine (15.8 g.) in chloroform (95 ml.) and the mixture was stirred and heated at 50° C. for 4 hours and then cooled and filtered. The solid residue (39 g. after washing with chloroform and drying) was added to a stirred mixture of ethanol (87.5 ml.) and concentrated aqueous hydrochloric acid (42.5 ml.) and the mixture was stirred at laboratory temperature for 17 hours, cooled to 5° C. and filtered. The solid product was washed with water and then with acetonitrile, and crystallised from methanol. There was thus obtained 2-m-nitrophenyl-2-oxoethylamine hydrochloride, m.p. 215° C. (with decomposition).

EXAMPLE 33

A mixture of methyl N-(2-m-cyanophenyl-2-oxoethyl)carbamate (15.42 g.), hydrazine hydrate (7.07 ml.), water (500 ml.) and ethanol (20 ml.) was heated under reflux for 15 hours, cooled and filtered and the solid product was crystallised from a 4:1 v/v mixture of ethanol and acetic acid. There was thus obtained 6-m-cyanophenyl-4,5-dihydro-2H-1,2,4-triazin-3-one, m.p. 278°–280° C.

The methyl N-(2-m-cyanophenyl-2-oxoethyl)carbamate (m.p. 125°–126° C.) used as starting material was obtained from m-cyanoacetophenone by a similar process to that described in the second part of Example 31 except that methyl chloroformate was used instead of ethyl chloroformate. The following intermediates were characterised by melting point:
m-cyanophenacyl bromide m.p. 67°–69° C.
m-cyanophenacyl azide m.p. 99°–101° C.
2-(m-cyanophenyl)-2-oxoethylamine hydrochloride, m.p. >360° C.

EXAMPLE 34

The process described in Example 33 was repeated except that the mixture was heated under reflux for only 3 hours and was then cooled and extracted three times with ethyl acetate (100 ml. each time). The combined extracts were dried and evaporated to dryness and the residue was crystallised from ethanol. There was thus obtained methyl N-(2-m-cyanophenyl-2-hydrazinoethyl)carbamate, m.p. 127°–129° C.

A mixture of the above compound (0.5 g.), acetonitrile (5 ml.) and aqueous 2N-sodium hydroxide solution (0.05 ml.) was stirred at laboratory temperature for 3 hours. 33% Aqueous sodium hydroxide solution (0.05 ml.) was added and the mixture was heated at 90° C. for 1 hour, cooled and filtered. The solid residue was crystallised from acetic acid and there was thus obtained 6-m-cyanophenyl-4,5-dihydro-2H-1,2,4-triazin-3-one, m.p. 278°–280° C.

EXAMPLE 35

The process described in Example 33 was repeated except that methyl N-(2-p-cyanophenyl-2-oxoethyl)carbamate was used as starting material in place of the m-isomer. There was thus obtained 6-p-cyanophenyl-4,5-dihydro-2H-1,2,4-triazin-3-one, m.p. 340° C. after crystallisation from dimethylformamide.

EXAMPLE 36

A mixture of N-[p-(2,3,4,5-tetrahydro-3-oxo-1,2,4-triazin-6-yl)phenyl]acetamide (Example 31; 1 g.) and aqueous 4N-hydrochloric acid (15 ml.) was heated under reflux for 25 minutes, cooled and filtered. The residue was dissolved in hot water and the solution was carbon treated, then made basic with aqueous sodium hydroxide solution, cooled and filtered. The solid product was crystallised from water and there was thus obtained 6-p-aminophenyl-4,5-dihydro-2H-1,2,4-triazin-3-one, m.p. 250°–251° C.

EXAMPLE 37

The process described in Example 4 was repeated except that 6-p-aminophenyl-4,5-dihydro-2H-1,2,4-triazin-3-one (Example 36) was used as starting material. There was thus obtained 1-methyl-3-p-(2,3,4,5-tetrahydro-3-oxo-1,2,4-triazin-6-yl)phenylurea, m.p. 337°–340° C. (with decomposition) after crystallisation from acetic acid.

EXAMPLE 38

A mixture of 6-m-cyanophenyl-4,5-dihydro-2H-1,2,4-triazine-3-one (Example 33; 5 g.) and a 30% w/v solution of potassium hydroxide in methanol (30 ml.) was stirred at 55° C. for 20 hours, water (100 ml.) was added and mixture was boiled and then filtered. The hot filtrate was acidified to pH 1 with concentrated aqueous hydrochloric acid and the mixture was filtered. The solid residue was purified by solution in aqueous potassium hydroxide solution and precipitation with concentrated aqueous hydrochloric acid, and was then crystallised from dimethylformamide. There was thus obtained m-(2,3,4,5-tetrahydro-3-oxo-1,2,4-triazin-6yl)-benzoic acid, m.p. >300° C.

The process described above was repeated except that the corresponding p-cyanophenyl-triazine (Example 35) was used as starting material. There was thus obtained p-(2,3,4,5-tetrahydro-3-oxo-1,2,4-triazin-6-yl)benzoic acid, m.p. 326°–328° C.

EXAMPLE 39

The process described in Example 15 was repeated except that m- or p-(2,3,4,5-tetrahydro-3-oxo-1,2,4-triazin-6-yl)benzoic acid (Example 38) and the appropriate alcohol, amine or ammonia were used as starting materials. There were thus obtained the compounds described in the following tables:

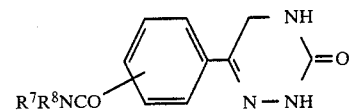

| $R^6$ | Position of Substituent | m.p. (°C.) | Crystallisation Solvent |
|---|---|---|---|
| methyl | m- | 212–215 | aqueous methanol |
| ethyl | m- | 188–191 | aqueous methanol |
| n-propyl | m- | 148–150 | ethyl acetate |
| methyl | p- | 262–264 | ethanol |
| ethyl | p- | 235–237 | ethyl acetate/diethyl ether |
| isopropyl | p- | 235–238 | methanol |

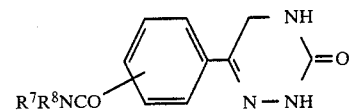

| $R^7$ | $R^8$ | Position of Substituent | m.p. (°C.) | Crystallisation Solvent |
|---|---|---|---|---|
| H | H | m- | >300 | dimethylformamide/diethyl ether |
| methyl | H | m- | 237–239 | methanol |
| ethyl | ethyl | m- | 184–186 | methanol |
| H | H | p- | 290–295 (d) | dimethylformamide/methanol |
| methyl | H | p- | 282–284 (d) | methanol |
| ethyl | H | p- | 310–312 | methanol |
| n-propyl | H | p- | 305–306 (d) | methanol |
| methyl | methyl | p- | 220–222 | methanol |
| —CH$_2$CH$_2$OCH$_2$CH$_2$— | | p- | 245–248 | aqueous methanol |

EXAMPLE 40

Hydrogen sulphide was bubbled for 90 minutes through a stirred solution of 6-p-cyanophenyl-4,5-dihydro-2H-1,2,4-triazine-3-one (Example 35; 1.0 g.) and triethylamine (1 ml.) in ethanol (50 ml.) which was maintained at 50° C., and the mixture was then cooled and evaporated to dryness under reduced pressure. The residue was crystallised from dimethylformamide and there was thus obtained p-(2,3,4,5-tetrahydro-3-oxo-1,2,4-triazin-6-yl)thiobenzamide, m.p. 292°–293° C. (with decomposition).

EXAMPLE 41

Sodium hydride (0.72 g. of a 50% dispersion in mineral oil) was added to a stirred solution of 6-m-cyanophenyl-4,5-dihydro-2H-1,2,4-triazin-3-one (Example 33; 3.0 g.) in dimethylformamide (50 ml.), and after the effervesence had ceased a solution of methyl iodide (0.94 g.) in dimethylformamide (5 ml.) was added during 15 minutes. The mixture was stirred for a further hour and then evaporated to dryness under reduced pressure. The residue was purified by chromatography on a silica gel (Merck 7734; 300 g.) column using a 19:1 v/v mixture of methylene chloride and methanol as eluant. There was thus obtained 6-m-cyanophenyl-4,5-dihydro-4-methyl-2H-1,2,4-triazin-3-one, m.p. 248°–251° C. after crystallisation from methanol.

EXAMPLE 42

The process described in Example 10 was repeated using p-(2,3,4,5-tetrahydro-3-oxo-1,2,4-triazin-6yl)benzoic acid (Example (Example 38) and either aqueous 2N-potassium hydroxide solution or liquid benzylamine as starting materials. There were thus obtained respectively the potassium salt (m.p. >300° C. after crystallisation from water) and the benzylamine salt (m.p. >300° C. after crystallisation from dimethylformamide) of said acid.

EXAMPLE 43

A mixture of N,N-dimethyl-p-(5,6-dihydro-5-oxo-4H-1,3,4-thiadiazin-2-yl)benzamide (Example 2; 0.231 g.) and aqueous 2N-sodium hydroxide solution (12 ml.) was stirred at laboratory temperature for 22 hours and then acidified with aqueous 2N hydrochloric acid and filtered. The solid product was crystallised from methanol and there was thus obtained p-(5,6-dihydro-5-oxo-4H-1,3,4-thiadiazin-2-yl)benzoic acid, m.p. 306°–308° C. (with decomposition).

What we claim is:

1. A heterocyclic compound of the formula:

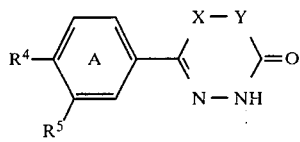

wherein X is —$CR^1R^2$— and Y is oxygen, wherein $R^1$, and $R^2$, which may be the same or different, each is hydrogen or alkyl of up to 4 carbon atoms; wherein $R^4$ and $R^5$, which may be the same or different, each is hydrogen, cyano, nitro, amino or hydroxy, or alkylthio of up to 4 carbon atoms, or has the formula:

wherein Q is a direct link, or is imino (—NH—), or is oxyalkylene of up to 4 carbon atoms, wherein Z is oxygen or sulphur and wherein $R^6$, $R^7$, $R^8$ and $R^9$, which may be the same or different, each is hydrogen, alkyl, alkenyl, cycloalkyl or alkoxyalkyl each of up to 6 carbon atoms, or aryl or arylalkyl each of up to 12 carbon atoms, or wherein $R^7$ and $R^8$ together with the adjacent nitrogen atom form a 5- or 6-membered fully-saturated heterocyclic ring, provided that $R^4$ and $R^5$ are not both hydrogen;

or wherein $R^4$ and $R^5$ are joined together such that with the benzene ring A they form a benzheterocyclic ring wherein the heterocyclic part is a 5- or 6-membered ring containing one oxygen, sulphur or nitrogen atom, and which heterocyclic part may optionally contain an oxo substituent or an alkyl or alkanoyl substituent each of up to 6 carbon atoms;

and wherein the benzene ring A bears no further substituent or bears one or more chloro, bromo, methyl, ethyl, methoxy or ethoxy substituents; or a salt thereof where appropriate.

2. A heterocyclic compound as claimed in claim 1 wherein
X is —$CH_2$ and Y is oxygen,
wherein $R^4$ is hydrogen, wherein $R^5$ is cyano and wherein ring A bears no further substituent.

3. A pharmaceutical composition comprising as active ingredient a cardiotonically effective amount of at least one heterocyclic compound, claimed in claim 1, in association with a pharmaceutically-acceptable diluent or carrier therefor.

4. A composition as claimed in claim 3 which contains, in addition to the heterocyclic compound, one or more drugs selected from sedatives, vasodilators, diuretics, cardiac membrane stabilising agents, agents used in the treatment of Parkinson's disease and other tremors, and cardiotonic agents.

5. A method for the treatment of acute or chronic heart failure in a warm-blooded animal in need of such treatment which comprises administering to said animal an effective amount of a heterocyclic compound claimed in claim 1.

* * * * *